United States Patent [19]
Birnboim

[11] Patent Number: 5,976,829
[45] Date of Patent: Nov. 2, 1999

[54] DUAL PURPOSE TISSUE FIXATIVE

[76] Inventor: Hyman C. Birnboim, 1552 Featherston Drive, Ottawa, Ontario, Canada, K1H 6P2

[21] Appl. No.: 08/708,056

[22] Filed: Aug. 30, 1996

Related U.S. Application Data

[63] Continuation of application No. 08/231,247, Apr. 22, 1994, abandoned.

[51] Int. Cl.$^6$ .................. C12Q 1/08; C12Q 1/00
[52] U.S. Cl. ............ 435/40.5; 435/40.52; 435/1.1; 424/75; 436/8; 436/17; 436/18
[58] Field of Search .................. 435/40.5, 40.52, 435/240.1, 1.1; 436/8, 17, 18; 424/75

[56] References Cited

U.S. PATENT DOCUMENTS

| | | | |
|---|---|---|---|
| 4,826,691 | 5/1989 | Prochnow | 426/1 |
| 4,857,300 | 8/1989 | Maksem et al. | 424/3 |
| 4,888,278 | 12/1989 | Singer et al. | 435/6 |
| 5,196,182 | 3/1993 | Ryan | 424/3 |
| 5,357,977 | 10/1994 | Michels | 128/758 |
| 5,389,549 | 2/1995 | Hamaguchi et al. | 436/10 |
| 5,405,606 | 4/1995 | Campbell et al. | 424/75 |

FOREIGN PATENT DOCUMENTS 1-140064  1/1989  Japan .

OTHER PUBLICATIONS

Eidus et al "A New Fixative for Molecular Biology and Diagnostic Pathology: Approximating a Universal Fixative" *FASEB J* 8(4–5) 1994 p. A391.

J. Histochem. & Cytochem. McAllister et al. vol. 33, No. 10 pp. 1026–1032 1985. Comparative Usefullness of Tissue Fixatives for In Situ Viral.

Exp. Hematol. Bramwell et al, 16:730–732, 1988. The Effects of Fixative Type and Fixation Time on the Quantity and Quality of Extractable DNA.

Am. J. Clin. Pathol. Greer et al. 95:117–124. 1991. PCR Amplification from Paraffin–Embedded Tissues.

Anatomic Pathology, Esteban et al. Apr. 1991, pp. 460–465; Effects of Various Fixatives and Fixation Conditions on DNA Ploidy Analysis.

Am. J. Hum. Genet. Barker et al. 39:661–668, 1986. High Molecular Weight DNA from Fixed Cytogenetic Preparations.

Anal. Biochem. Smith, et al. 160:135–138, 1987. Extraction of Cellular DNA from Human Cells and Tissues fixed in Ethanol.

J. Histochem & Cytochem. Ben–ezra et al.1991 vol. 39. No. 3 pp. 351–354 Effect of Fixation on the Amplification of Nucleic acids from Paraffin.

J. Histochem. & Cytochem. WEiss et al. 1991 vol. 39 No. 9 pp. 1237–1242 Effects of Different Fixatives on Detection of Nucleic Acids from.

Arch. Pathol. Lab. Med., Bostwick, D.G., vol. 118, pp. 298–302 1994. Establishment of the Formalin–Free Surgical Pathology Laboratory.

*Primary Examiner*—Paula K. Hutzell
*Assistant Examiner*—Heather A. Bakalyar
*Attorney, Agent, or Firm*—Lorusso & Loud

[57] ABSTRACT

A dual purpose tissue fixative is described. The fixative comprises a cross-linking aldehyde, alcohol, a chelating agent and a non-amine buffer. More particularly, the tissue fixative comprises 0.1–2% w/v formaldehyde, 45–90% w/w alcohol, 1–10 mM of a chelating agent and 1–50 mM of a non-nitrogen buffer. The tissue fixative permits the recovery of high molecular weight DNA and RNA from the tissue sample for molecular genetic analysis. The tissue fixative also preserves the morphology and immunogenicity of the tissue allowing for pathology analysis. The tissue fixative is compared to 95% alcohol and a standard fixative as 10% BNF.

8 Claims, 6 Drawing Sheets

DUAL PURPOSE TISSUE FIXATIVE

This application is a continuation of U.S. application Ser. No. 08/231,247, filed Apr. 22, 1994, now abandoned.

FIELD OF THE INVENTION

The present invention relates to a dual purpose tissue fixative. The tissue fixative permits the recovery of high molecular weight nucleic acids (DNA and RNA) from the tissue sample for molecular genetic analysis. The fixative also preserves the morphology and immunogenicity of the tissue allowing for pathology analysis.

BACKGROUND OF THE INVENTION

The analysis of tissue samples removed at surgery or autopsy can reveal important clues in our understanding of various pathological states. For example, the analysis of the DNA obtained from tumor biopsy can provide valuable insight into the genetic defects that underlie malignant transformation. Freshly obtained samples must immediately be stored in a tissue fixative in order to prevent decomposition. The ideal fixative should (i) permit recovery of high molecular weight nucleic acids (DNA and RNA) from the sample for molecular analysis and (ii) preserve the morphology and lmmunogenicity of specimens allowing routine anatomical pathology investigation.

A commonly used fixative is 10% buffered neutral formalin (BNF). Samples stored in BNF are adequate for pathology analysis. However BNF degrades nucleic acids and therefore samples are not useful for the extraction of high molecular weight DNA or RNA. Solutions of 95% ethanol have been shown to be effective in preserving DNA in a limited number of cases. However, samples stored in 95% ethanol are not satisfactory for the pathologist. Consequently, when one wants to obtain samples for both DNA extraction and pathology it is necessary to take the fresh biopsy sample and store part of it in BNF and another part in, for example, liquid nitrogen. This conventional method requires that a technician is on call during surgery in order to properly store the sample.

Therefore, in view of the foregoing it is desirable to develop a tissue fixative that permits the recovery, weeks or even months after fixation, of high molecular weight nucleic acids for molecular genetic analysis, while at the same time preserving the morphology of the sample for analysis by the pathologist.

SUMMARY OF THE INVENTION

The present invention solves the problem of the prior art fixatives as it allows the recovery of substantially intact nucleic acids (both DNA and RNA) from a tissue sample and also adequately preserves the sample for pathological analysis.

In particular, the present invention provides a tissue fixative comprising:
- a cross-linking aldehyde;
- alcohol;
- a chelating agent; and
- a non-nitrogen containing buffer.

More particularly, the tissue fixative comprises about:
- 0.1–2% w/v formaldehyde;
- 45–90% w/w alcohol;
- 1–10 mM of a chelating agent; and
- 1–50 mM of a non-nitrogen-containing buffer.

The aldehyde is selected from those capable of cross-linking proteins. The aldehyde may be selected from, for example, formaldehyde, gluteraldehyde, and the like.

The alcohol is preferably a low molecular weight alcohol such as methanol or ethanol. The alcohol may also be composed of a mixture of two or more alcohols. In a preferred embodiment, the alcohol is methanol.

The chelating agent is preferably one that is soluble in alcohol and has a high affinity for divalent cations in tissue. A preferred chelating agent is trans-1-2-diaminocyclohexane-N,N,N',N'-tetraacetic acid (CDTA).

The non-nitrogen containing buffer is preferably a phosphate buffer such as potassium or sodium phosphate or mixtures thereof. The buffer should act to control the pH of the tissue sample during fixation. In a preferred embodiment, the buffer maintains the pH of the sample from about 6.0 to about 8.5, since acidic agents can cause depurination and breakdown of the nucleic acids. More preferably, the buffer should maintain the sample at a pH of about 7.3.

In a more preferred embodiment, the tissue fixative comprises about:
- 0.75% w/v formaldehyde;
- 55% w/w methanol;
- 5 mM trans-1-2-diaminocyclohexane-N,N,N',N'-tetraacetic acid (CDTA); and
- 15 mM potassium phosphate and 15.8 mM sodium phosphate as buffer.

BRIEF DESCRIPTION OF THE DRAWINGS

FIG. 6 represents stained sections of an invasive carcinoma of the colon.

DETAILED DESCRIPTION OF THE INVENTION

EXAMPLE 1

Preparation of Preferred Fixative

The preparation of a preferred tissue fixative according to the present invention is described below. Each of the components of the fixative may be obtained for example as described below:

1) 10% neutral buffered formalin, Anachemia Cat. No. R2400. (Composition/1000 ml: 100 ml of 37% formaldehyde, 4 g sodium phosphate monobasic, 6.5 g sodium phosphate dibasic)
2) Methanol, Fisher Cat. No. A412B.
3) CDTA, Sigma Cat. No. D1383, Trans-1-2-diaminocyclohexane-N,N,N',N'-tetraacetic acid, F.W. 346.3.
4) Potassium phosphate, dibasic, anhydrous. $K_2HPO_4$, F.W. 174.18, Fisher, Cat. No. P-288.

The CDTA chelator and potassium phosphate buffer are first prepared together as follows:

1) Add 3 L of $ddH_2O$ to a 4 L Winchester, with glass funnel.
2) Weigh out 53.56 g of $K_2HPO_4$ and 35.5 g CDTA in plastic weighing boats. Transfer to Winchester with powder funnel. Rinse funnel and weighing boats with 1.1 L $ddH_2O$ into Winchester.
3) Cap and shake by hand until all solute dissolves.
4) Measure pH of a 5 mL sample of solution.

This combined solution is designated "CKP".

The tissue fixative is prepared in a 40 L carboy as follows:

1) Add 24 L Methanol, to the 24 L mark.
2) Add 8 L of 10% neutral buffered formalin, using a 2 L cylinder.
3) Add 8 L CKP solution using a 2 L cylinder.
4) Mix with a stirring paddle for 3 min.
5) Remove 25 mL and dilute with 25 mL water. Save for measurement of pH using pH meter within 1 hour.

Final Concentrations:

| | |
|---|---|
| Methanol | 55% (w/v) |
| Formaldehyde | 0.75% (w/v) |
| $K_2HPO_4$ | 15.0 mM |
| Na phosphate | 15.8 mM |
| CDTA | 5 mM |

Final pH of 1:1 dilution in water = 7.3

EXAMPLE 2

Preparation of Other Fixatives

Several other fixatives according to the present invention were also prepared. The stock reagents used were as follows:

1. 6.7 M Formaldehyde. Commercial "37%" formaldehyde is 13.3 M in 10–14% methanol. Immediately before use, dilute 12.5 mL of 13.3 M formaldehyde in 12.5 mL of water to make 6.7 M formaldehyde. Boil gently in a 60 mL Erlenmeyer flask in the fume hood for 5 min to degrade paraformaldehyde. Cool to room temperature.
2. Methanol.
3. Ethanol.
4. DMF. Dimethylformamide.
5. CDTA (0.5 M, pH 7.0). Chelating agent. Cyclohexane diamine-tetraacetate.
6. Phosphate buffer. pH 6.8. Prepared by mixing equal volumes of 1 M $NaH_2PO_4$ and 1 M $Na_2HPO_4$.
7. Postassium phosphate dibasic buffer. $K_2HPO_4$.

The various fixatives shown in Table 1 were prepared by mixing the stock solutions according to the procedure in Example 1. The resulting concentrations of each of the components are shown in Table 1. These fixatives were tested and shown to be useful.

EXAMPLE 3

Comparison of Dual Purpose Fixative With Other Fixatives

Figure 1:
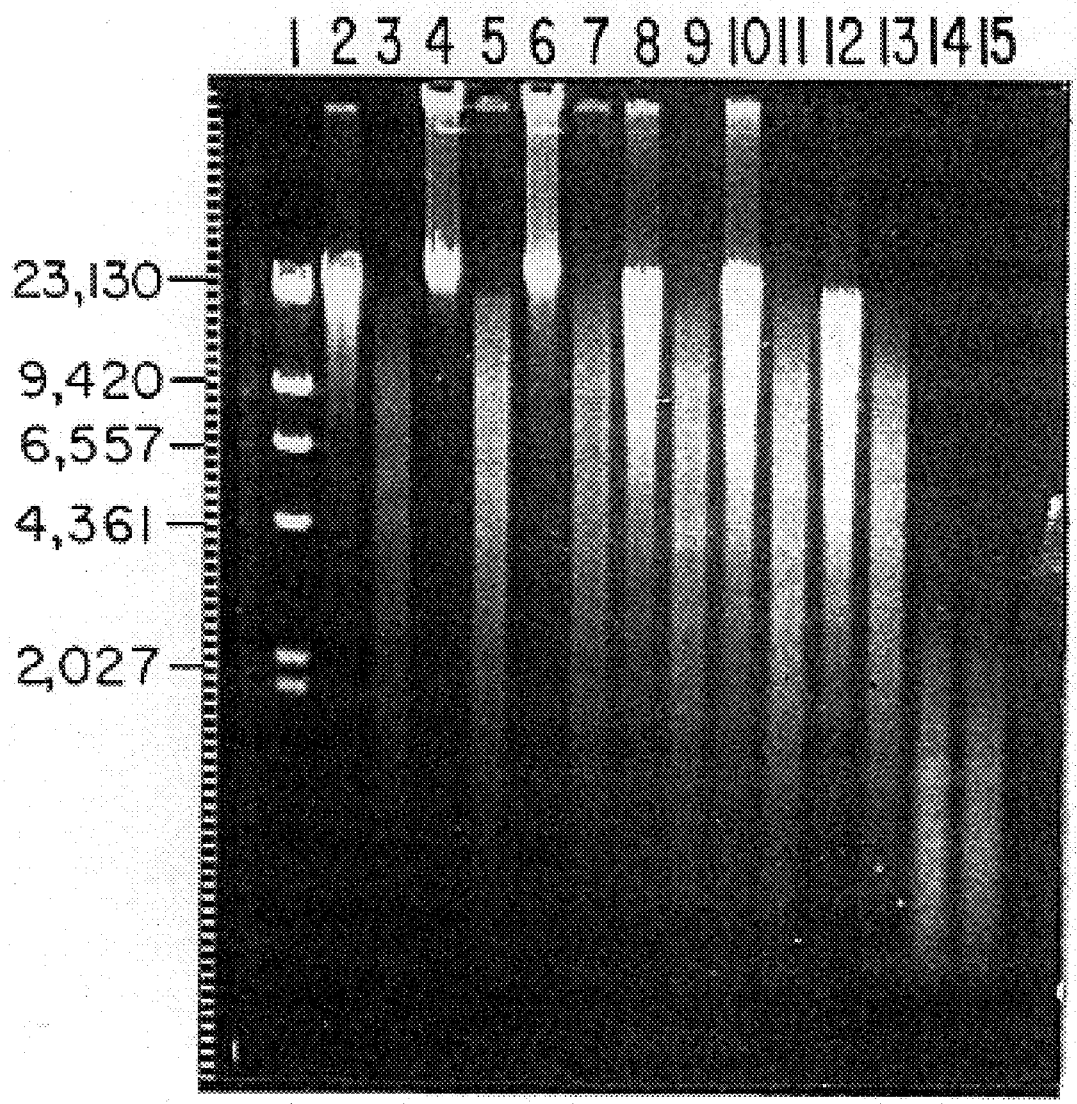
FIG. 1 represents agarose gels showing the comparison of the high molecular weight DNAs and their EcoR1 sensitivity when extracted from a colonic adenocarcinoma and variously fixed for different time periods.

The integrity of the DNA extracted from Duke's B3 colonic adenocarcinoma was compared from samples fixed in the tissue fixative prepared in Example 1 versus samples fixed in 95% alcohol or 10% BNF. Samples of surgically removed carcinoma were placed in each of the three fixatives. DNA was extracted from the samples at 3 days and at 8 months. The DNA was extracted using a method developed by the present inventor and described in Methods in Enzymology (1992) 216:154–159. Briefly, the DNA is extracted using proteinase K digestion and phenol-chloroform extraction in the presence of an amine. Portions of the DNA were digested with the restriction enzyme EcoR1. One microgram of the DNA was applied to a 0.8% agarose gel in 40 mM Tris buffer containing 20 mM sodium acetate, 1 mM CDTA. The results are shown in FIG. 1 in which:

Lane 1 contains molecular weight markers.
Lane 2 contains DNA extracted from an unfixed sample.
Lane 3 contains DNA digested with EcoR1.
Lane 4 contains DNA extracted from a sample fixed in ethanol for three days.
Lane 5 contains DNA extracted from a sample fixed with ethanol for three days and digested with EcoR1.
Lane 6 contains DNA extracted from a sample fixed with the Example 1 fixative for three days.
Lane 7 contains DNA extracted from a sample fixed with the Example 1 fixative for three days and digested with EcoR1.
Lane 8 contains DNA extracted from a sample fixed with formalin for three days.
Lane 9 contains DNA extracted from a sample fixed with formalin for three days and digested with EcoR1.
Lane 10 contains DNA extracted from a sample fixed in ethanol for eight months.
Lane 11 contains DNA extracted from a sample fixed with ethanol for eight months and digested with EcoR1.
Lane 12 contains DNA extracted from a sample fixed with the Example 1 fixative for eight months.
Lane 13 contains DNA extracted from a sample fixed with the Example 1 fixative for eight months and digested with EcoR1.
Lane 14 contains DNA extracted from a sample fixed with formalin for eight months.
Lane 15 contains DNA extracted from a sample fixed with formalin for eight months and digested with EcoR1.

The results indicate that DNA extracted from a sample fixed in the Example 1 fixative shows a similar profile as DNA extracted from samples fixed in ethanol. Both yield high molecular weight, EcoR1 digestible DNA. Samples fixed in BNF clearly demonstrate extensive DNA degradation.

EXAMPLE 4

PCR Amplification of the Ki-ras Oncogene from DNA Extracted from Fixed Samples

Portions of a surgically obtained rectal mucosa were fixed in each of the Example 1 fixative, 10% BNF and ethanol for four months. DNA was extracted from each sample as described in Example 3. The extracted DNA was subjected to 30 cycles of PCR amplification with primers for the Ki-ras cellular oncogene.

Figure 2:
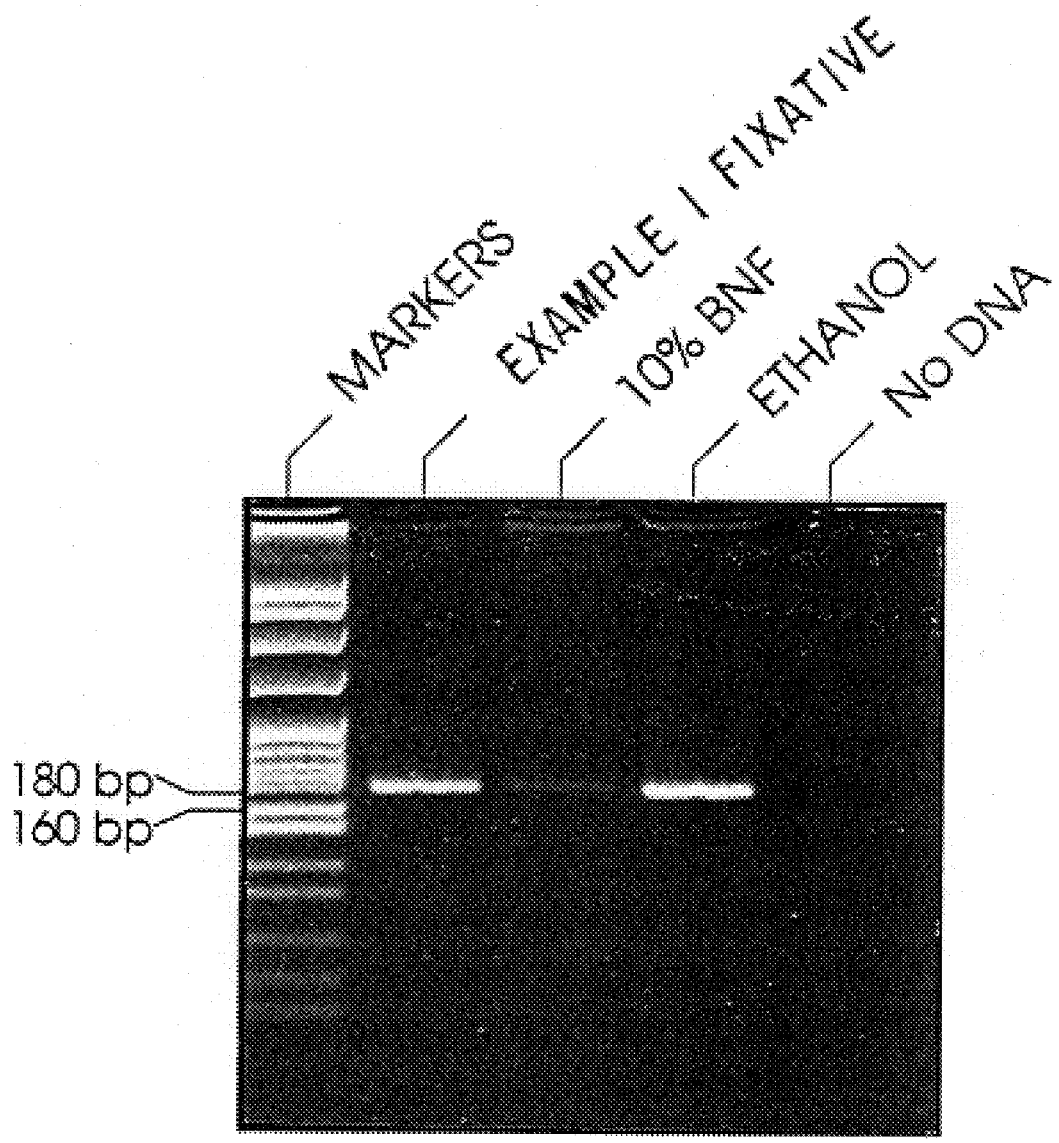
FIG. 2 represents agarose gels illustrating a Ki-ras gene fragment obtained by PCR amplification of DNA extracted from rectal mucosa specimens that were fixed for four months in various fixatives.

The results, shown in FIG. 2, demonstrate that DNA extracted from samples fixed in the Example 1 fixative are amenable to PCR amplification as evidenced by the presence of the 174 bp Ki-ras oncogene in the sample. Samples fixed in BNF did not yield any PCR amplification product.

EXAMPLE 5
Total Nucleic Acid Analysis of Fixed Rat Livers

Figure 3:
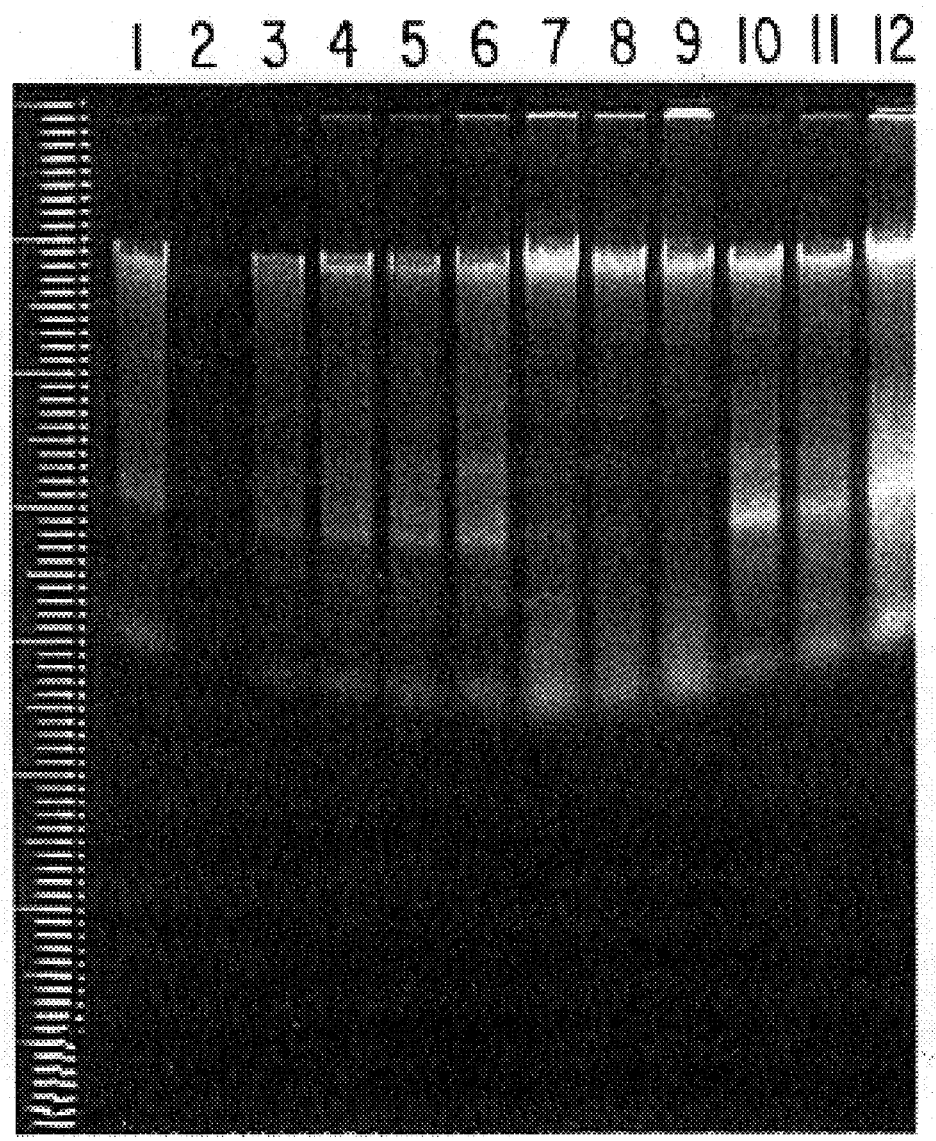
FIG. 3 represents agarose gels showing the total nucleic acid extracted from rat livers fixed for four weeks in the fixative of the present invention after various extraction procedures.

An intact rat liver was fixed for four weeks in the Example 1 fixative. Two hundred mg wet weight portions were removed and the DNA was extracted by 3 variations of the nucleic acid extraction procedure. The extraction procedures differed with respect to the pH of the extracting solution. Solution 1 had a pH of 7.2, solution 2 had a pH of 8.0 and solution 3 had a pH of 6.8. The extracted nucleic acid was applied to a 1.2% agarose gel in 10 mM phosphate buffer in triplicate. The results are shown in FIG. 3. Lanes 1–6 represents samples extracted in solution 1, Lanes 7–9 represent samples extracted in solution 2 and Lanes 10–12 represents samples extracted in solution 3. The top band in each sample represents DNA, while the lower two bands represent RNA. The results indicate that nucleic acids, including RNA, can be extracted for up to four weeks after tissue fixation in the Example 1 fixative. Extracting the nucleic acids at a pH between about 6.5 and 7.0 is optimal for the extraction of RNA from the samples.

Figure 4A:
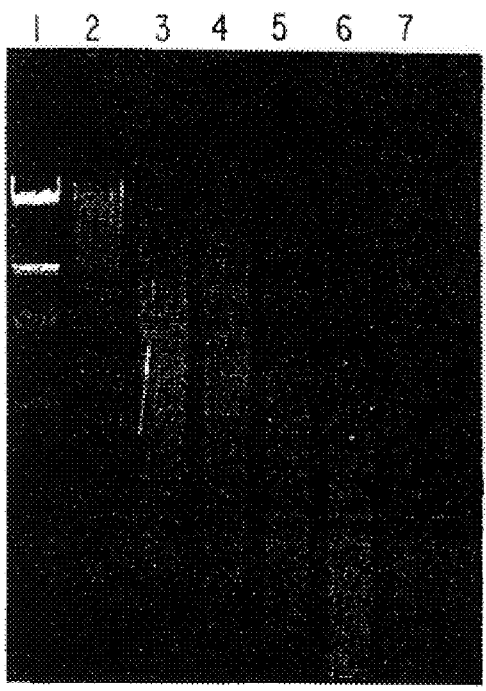
FIG. 4A represents agarose gels showing DNA extracted from samples fixed in 10% BNF, at various time points.
Figure 4B:
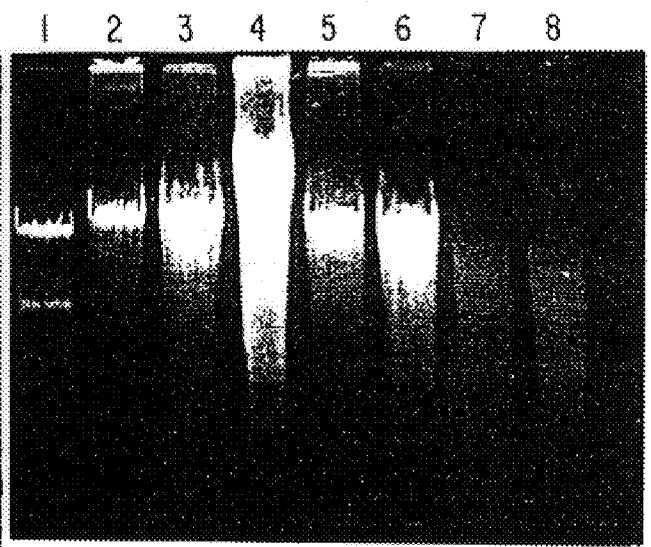
FIG. 4B represents agarose gels showing DNA extracted from samples fixed in the fixative of the invention, at various time points.

EXAMPLE 6
Comparison of the Present Fixative and 10% BNF on DNA Degradation Samples of a modified Duke's C2 colonic adenocarcinoma were placed in the Example 1 fixative or in 10% BNF. At various time points, DNA was extracted from the samples as described previously. The samples were electrophoresed on an agarose gel as shown in FIG. 4. FIG. 4A represents DNA from samples fixed in 10% BNF and FIG. 4B represent DNA from samples fixed in the Example 1 fixative. The lanes are as follows Lane 1: phage DNA Hind III digest
Lane 2: DNA extracted from a sample fixed for 3 days
Lane 3: DNA extracted from a sample fixed for 1 week
Lane 4: DNA extracted from a sample fixed for 2 weeks
Lane 5: DNA extracted from a sample fixed for 1 month
Lane 6: DNA extracted from a sample fixed for 2 months
Lane 7: DNA extracted from a sample fixed for 4 months
Lane 8: DNA extracted from a sample fixed for 8 months (FIG. 4B only)

The results indicate that DNA obtained from samples fixed in 10% BNF was extensively degraded after one week in the fixative. On the other hand, the DNA extracted from samples fixed in the present fixative remained intact for several months.

EXAMPLE 7
Pathological Analysis of Samples fixed in the Present Fixative

Figure 5A:
FIG. 5A represents a resected segment of a human colon fixed in the fixative of the present invention.
Figure 5B:
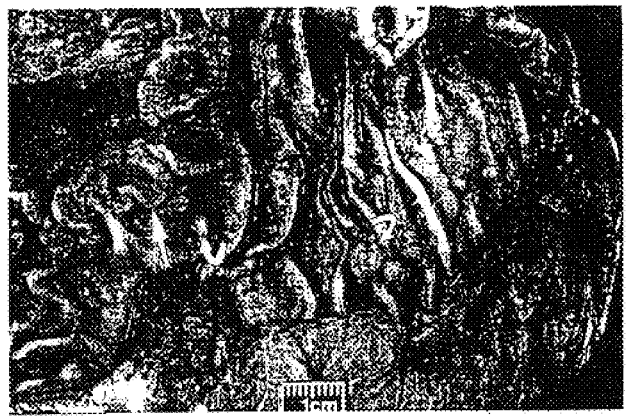
FIG. 5B is the same as FIG. 5A but at a higher magnification.

A resected segment of a human colon was fixed for 1 week in the Example 1 fixative and photographed as shown in FIG. 5. The photograph demonstrates that a sample fixed in the fixative according to the invention appears as if it was freshly resected. In contrast, it is known that samples fixed in formaldehyde turn grey in color. Samples fixed In alcohol have the disadvantage that they become brittle and difficult to handle. The results of FIG. 5 show that samples fixed in the fixative according to the invention better maintain the gross morphological properties of the tissue.

Figure 6A:
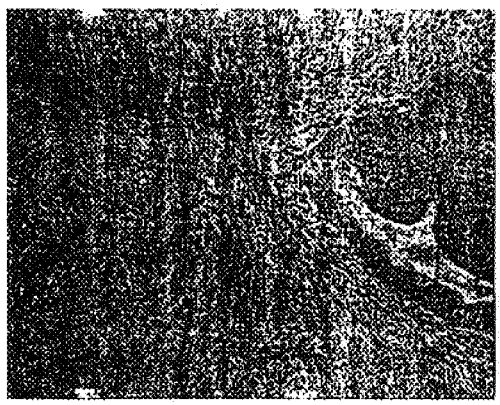
FIG. 6A represents a sample fixed in 10% BNF and FIG. 6B represents a sample fixed in the fixative of the present invention.
Figure 6B:
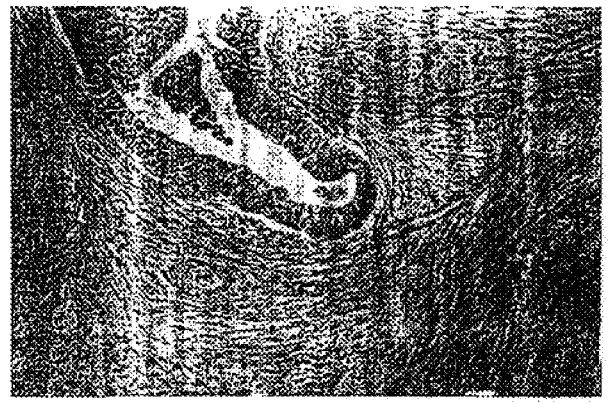

EXAMPLE 8
Comparison of Tissue Sections Fixed with the Present Fixative versus 10% BNF Haematoxylin and eosin stained sections of an invasive carcinoma of the colon had been fixed in either 10% BNF or the Example 1 fixative. The results are shown in FIG. 6 wherein FIG. 6A represents tissue fixed in 10% BNF and FIG. 6B represents tissue fixed in the Example 1 fixative. The results illustrate that samples fixed in the Example 1 fixative are indistinguishable histologically from sections preserved in BNF.

EXAMPLE 9
Immunoreactivity Profile of Tissue Fixed in Various Fixatives

A human colorectal cancer sample was portioned and separate samples were fixed in each of 10% BNF, ethanol and the Example 1 fixative. The samples were fixed from periods ranging from three days to two months. The samples were tested for the presences of various antigens using commercially available antibodies. The results, shown in Table 2, indicate that samples fixed in the Example 1 fixative show similar immunoreactivity profiles. Furthermore, the immunoreactivity compared favorably with that obtained in samples fixed in alcohol based fixatives, such as Carnoys.

EXAMPLE 10
Quantitation of DNA Obtained from Samples

Samples of a human colorectal cancer and an ulcerative colitis were stored in either the Example 1 fixative or 10% BNF. DNA was extracted from the samples as described previously. The amount of DNA was determined spectrophotometrically. The results, shown in Table 3, demonstrate that the total recovery of DNA is greater from samples fixed in the Example 1 fixative versus samples fixed in 10% BNF.

Summary

The above experiments demonstrate that the fixative according to the present invention is capable of preserving the DNA and RNA in tissue samples for up to several months or longer. The results also indicate that samples fixed in the present fixative are morphologically similar to freshly obtained samples and are useful for analysis by the pathologist.

While the above described examples 3–10 use the fixative as prepared in Example 1, it is to be appreciated that various modifications can be made to the tissue fixative and still be within the scope of the present invention. For example, the percentages of the various components can be varied as described in Example 2 and still produce a useful fixative. Furthermore, additional ingredients such as dimethylformamide, formamide, dimethylsulfoxide or ethylene glycol may also be added to the fixative. Other additives may include low concentrations of detergents or other organic solvents.

TABLE 1

COMPOSITION OF COLON CANCER FIXATIVES

| STOCK REAGENTS | FIXATIVE | | | | | | |
| --- | --- | --- | --- | --- | --- | --- | --- |
|  | #1 | #2 | #3 | #4 | #5 | #6 | #7 |
| Formaldehyde 13.3M (w/v) | 0.75% | 1.5% | 0.75% | 1.5% | 0.75% | 0.75% | 0.75% |
| Methanol (w/w) |  | 55% | 75% | — | — | 75% | 55% | 55% |

TABLE 1-continued

COMPOSITION OF COLON CANCER FIXATIVES

| STOCK REAGENTS | FIXATIVE | | | | | | |
|---|---|---|---|---|---|---|---|
| | #1 | #2 | #3 | #4 | #5 | #6 | #7 |
| Ethanol (w/w) | — | — | 55% | 75% | — | — | — |
| CDTA (mM) | 5 | 5 | 5 | 5 | 5 | 5 | 5 |
| DMF (v/v) | 10% | 10% | 10% | 10% | 20% | — | 10% |
| Na-Phosphate Buffer (mM) | 20 | 20 | 20 | 20 | 20 | 20 | 20 |
| Potassium Phosphate (mM) | — | — | — | — | — | 5 | 5 |

TABLE 2

IMMUNOREACTIVITY PROFILES OF HUMAN COLORECTAL CANCER SPECIMENS PROFILE FOR FIXATION IN EXAMPLE I FIXATIVE versus STANDARD FIXATIVES

| SAMPLE | FIXATIVE | ANTIGEN | | | | | | | | | | |
|---|---|---|---|---|---|---|---|---|---|---|---|---|
| | | LMWK | HMWK | CHR | PSA | PAP | VIM | HMB 45 | S100 | MSA | CEA | CEA-D14 |
| 1 | 10% BNF | 4+ | ± | 3+ (E) <br> − (T) | − | − | 3–4+ | − | 3+ | 3+ | ND | 2–3+ |
| 2 | Ethanol | 3–4+ | 3+ | ND | − | − | 4+ | ± | 2+ | 3+ | 3+ | 2+ (Ep) <br> 1+ (M) |
| 3 | EXAMPLE I FIXATIVE | 2–3+ | 1+ | 3–4+ (E) <br> − (T) | − <br> − | − <br> − | 3+ (M) <br> 1+ (Ep) | ± | 4+ | 4+ | 3+ | 4+ |
| 4 | EXAMPLE I FIXATIVE | 2–3+ | 2–3+ | 4+ (E) <br> − (T) | − | − | 3–4+ (M) <br> 1+ (Ep) | ± | 4+ | 3–4+ | 4+ | 3+ |
| 5 | EXAMPLE I FIXATIVE | 2–3+ | 2–3+ | 4+ (E) <br> − (T) | − | − | 3–4+ (M) <br> 1+ (Ep) | − | 3+ | 4+ | 3–4+ | 2–3+ (Ep) <br> 1+ (M) |

LMWK: Low molecular weight keratin
HMWK: High molecular weight karatin
CHR: Chromogranin
PSA: Prostate specific antigen
PAP: Prostatic Acid Phosphatase
VIM: Vimentin
HMB: Human Melanoma Specific Antigen
S100: S100 Protein
MSA: Muscle Specific Actin
CEA: Carcinoembryonic antigen
CEA-D14: Carcinoembryonic antigen
E: Endocrine cells
Ep: Epithelial cells
M: Muscle
T: Tumour
XXXX: Spurious reaction
ND: Not determined

TABLE 3

QUANTITATION OF PURE, HIGH MOLECULAR WEIGHT DNA FROM HUMAN LARGE BOWEL (SURGICAL SAMPLES) COMPARISON OF EXAMPLE I FIXATIVE AND 10% BNF FIXATIVE
DNA Recovered (μg/mg wet weight)[a]

| Clinical Diagnosis (specimen) | Example I Fixative | 10% BNF[b] |
|---|---|---|
| 1. Colorectal cancer | | |
| Normal tissue | 1.99 ± 0.26 (n = 10)[1] | 1.16 ± 0.30 (n = 4)[2] |
| Malignant tumour | 3.60 ± 0.29 (n = 18)[4] | 1.88 ± 0.18 (n = 12)[1,3] |
| 2. Ulcerative colitis | | |
| Normal tissue | 2.35 ± 0.20 (n = 12)[1] | 1.45 ± 0.09 (n = 4)[2] |
| Involved tissue Averages | 3.14 ± 0.21 (n = 11)[4] | 2.26 ± 0.30 (n = 4)[1,3] |
| All samples[c] | 2.89 ± 0.16 (n = 51)[5] | 1.75 ± 0.13 (n = 24)[6] |

[a]Statistical comparisons. Unlike superscripts denote statistically significant differences within each diagnostic group.
[b]10% BNF = 10% Buffered Neutral Formalin fixative.
[c]Recovery ot DNA from Example I fixed tissue greater than from 10% BNF fixed tissue (p 0.005).

What I claim as my invention is:

1. A tissue fixative comprising:
a protein cross-linking aldehyde;
alcohol;
CDTA as a chelating agent; and
a phosphate buffer.

2. A tissue fixative according to claim 1 comprising:
about 0.1–2% w/v of the aldehyde;
alcohol;
about 1–10 mM of the CDTA chelating agent; and
about 1–50 mM of the phosphate buffer.

3. A tissue fixative according to claim 1 comprising:
0.75% w/v formaldehyde;
55% w/v methanol;
5 mM of the CDTA chelating agent; and
15 mM potassium phosphate and 15.8 mM sodium phosphate as the buffer.

4. A tissue fixative according to claim 3 wherein the pH is approximately 7.3.

5. A tissue fixative according to claim 1 wherein the pH is approximately 7.3.

6. A tissue fixative according to claim 2 wherein the pH is approximately 7.3.

7. A tissue fixative according to claim 1 wherein the pH is approximately 6.0–8.5.

8. A tissue fixative according to claim 2 wherein the pH is approximately 6.0–8.5.

* * * * *